United States Patent [19]

Noyori et al.

[11] Patent Number: 4,578,482

[45] Date of Patent: Mar. 25, 1986

[54] PROCESS FOR PREPARING PROSTACYCLINS

[75] Inventors: Ryoji Noyori; Masaaki Suzuki; Akira Yanagisawa, all of Aichi; Seizi Kurozumi, Tokyo, all of Japan

[73] Assignee: Teijin Limited, Osaka, Japan

[21] Appl. No.: 563,835

[22] Filed: Dec. 21, 1983

[30] Foreign Application Priority Data

Dec. 23, 1982 [JP] Japan ................................. 57-224878
Dec. 28, 1982 [JP] Japan ................................. 57-227332

[51] Int. Cl.[4] ........................................ C07D 307/935
[52] U.S. Cl. ..................................... 549/214; 549/305; 549/415; 549/465; 544/153; 546/196; 548/525
[58] Field of Search ............... 549/465, 214, 415, 305; 546/196; 548/525; 544/153

[56] References Cited

PUBLICATIONS

Suzuki et al., Tet. Letters, 24 (11), pp. 1187–1188 (Mar. 1983).
Riediker et al., J.A.C.S. 104, pp. 5842–5844 (1982).
Bach et al., J. Org. Chem. 47, pp. 3707–3712 (1982).

*Primary Examiner*—Henry R. Jiles
*Assistant Examiner*—Bernard I. Dentz
*Attorney, Agent, or Firm*—Sughrue, Mion, Zinn, Macpeak, and Seas

[57] ABSTRACT

A process for producing prostacyclins of the formula

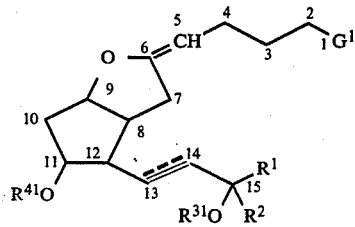

wherein the symbol ==== $G^1$, $R^1$, $R^2$, $R^{31}$ and $R^{41}$ are as defined in claim 1, which comprises reacting 5,6-dehydroprostaglandins $F_2$ of the formula

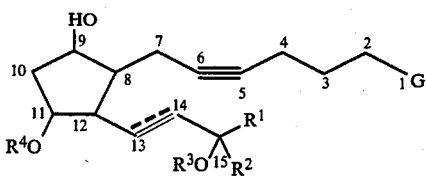

wherein the symbol === G, $R^1$, $R^2$, $R^3$ and $R^4$ are as defined in claim 1, with a mercury (II) compound in an inert organic solvent in the presence of tri($C_1$–$C_6$)alkylamine, treating the reaction product with a boron hydride compound, and if necessary, subjecting the reaction product to deprotecting reaction, hydrolysis reaction, or salt-forming reaction.

This process is industrially advantageous process for the preparation of prostacyclin and its derivatives.

13 Claims, No Drawings

PROCESS FOR PREPARING PROSTACYCLINS

BACKGROUND OF THE INVENTION

1. Field of the Invention

The present invention relates to a novel process for preparing prostacyclins. More particularly, the present invention relates to a process for preparing prostacyclins, which are useful as medicines, at a high efficiency by allowing 5,6-dehydroprostaglandins $F_2$ used as material compound to react with a mercury (II) compound in the presence of trialkylamine and treating the reaction product with a boron hydride compound.

2. Description of the Prior Art

Prostacyclin is a valuable and attracting substance in the medical and pharmaceutical field not only as a very useful medicine because of its beneficial physiological actions such as inhibition of platelet aggregation, vasodilation, antitumor action, antiasthmatic action, and anticancerous action, but also as a regulator of cell function in a living body.

However, the process for the preparation of prostacyclin requires the utmost caution throughout the course of its process since the enol ether structure contained in its skeleton is apt to be readily hydrolyzed under the neutral or acidic conditions, and several processes have already been proposed.

To the best knowledge of the inventors of this invention, the following three processes for the preparation of prostacyclin are publicly known:

(1) a process of obtaining prostacyclin by cyclization accompanied with halogenation of $PGF_{2\alpha}$ (see E. J. Corey et al., Amer. Chem. Soc., 99, 2006 (1977); R. A. Johnson et al., J. Amer. Chem. Soc., 100, 7690 (1978), etc.).

(2) A process of obtaining it by aldol condensation between cyclopentenylacetaldehyde derivative and cyclopentanoneenolate (see R. F. Newton et al., J. Chem. Soc., 922 (1981)).

(3) A method of obtaining it from $PGH_2$ by use of biological substance which contains biosynthetic enzyme of prostacyclin (see S. Moncada et al., Nature, 263, 633 (1976); R. A. Sbidgel et al., Prostaglandins, 16, 1 (1978)).

These processes, however, have the following drawbacks when studied from the viewpoint of producing prostacyclin on an industrial scale. Process (1) has a difficulty in that it uses costly $PGF_{2\alpha}$ as starting material which has to be prepared from Corey lactone through many processes. Process (2) has a problem that four stereoisomers are formed in said aldol condensation and they have to be separated, and only dl modification can be obtained according to the method proposed in the abovementioned document. (Process (3) utilizes a biological procedure and accordingly has a difficulty in obtaining prostacyclin in large quantity and a demerit of using unstable $PGH_2$ as a starting material. There is, of course, a method in which $PGH_2$ can be formed intermediately from arachidonic acid; however, arachidonic acid is also an unstable unsaturated fatty acid, costly, and not readily available. Therefore, all the three processes mentioned above are not satisfactory methods of preparing prostacyclins on an industrial scale.

The Journal of Americal Chemical Society, 104, 5842-5844 (1982) presents a method in which acetylenic alcohol is first allowed to react with mercury trifluoroacetate, then treated with lithium iodine to carry out the cyclization reaction, thus obtaining a corresponding enol ether. However, what is cited in this document is nothing but a compound which is akin to prostacyclin but differs from prostacyclin in having no functional group and therefore being much simpler in structure.

SUMMARY OF THE INVENTION

The object of the present invention is to provide an industrially advantageous process for the preparation of prostacyclin and its derivatives.

Another object of the present invention is to provide an industrially advantageous process for the preparation of prostacyclins by use of starting material which are readily obtainable on the chemical synthesis.

Still another object of the present invention is to provide an industrially advantageous process for the preparation of various derivatives of prostacyclin.

Further objects and advantages of the present invention will become apparent from the following description.

These objects and advantages of the present invention can be achieved by a process for the preparation of prostacyclins comprising the reaction of 5,6-dehydroprostaglandins $F_2$ expressed by the following formula (I)

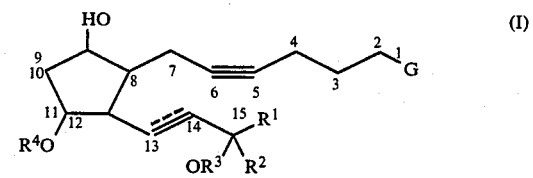

wherein the symbol ==== between the 13- and 14-positions indicates that a double or triple bond exists between the 13- and 14-positions; G represents $—COOR^5$ or $—CONR^6R^7$ in which $R^5$ represents a $C_1$–$C_{10}$ alkyl group, a substituted or unsubstituted phenyl group, a substituted or unsubstituted alicyclic group, a substituted or unsubstituted phenyl ($C_1$–$C_2$) alkyl group or a tri($C_1$–$C_7$)hydrocarbon-silyl group, $R^6$ and $R^7$ are identical or different and each represents a $C_1$–$C_{10}$ alkyl group, or taken together with the nitrogen atom to which they are bonded may form a substituted or unsubstituted 5- or 6-membered ring which may include a hetero atom; $R^1$ represents a hydrogen atom, a methyl group, or a protected ethynyl group; $R^2$ represents an unsubstituted $C_5$–$C_8$ alkyl group, a $C_1$–$C_5$ alkyl group substituted by a substituent selected from phenyl, phenoxy, $C_1$–$C_6$ alkoxy and $C_5$–$C_6$ cycloalkyl, which substituent may be substituted, or a substituted or unsubstituted alicyclic group, $R^3$ and $R^4$ are identical or different and each represents a $C_2$–$C_7$ acyl group, a tri($C_1$–$C_7$)hydrocarbon-silyl group or a group forming an acetal linkage together with the oxygen atom of the hydroxyl group, with a mercury (II) compound in an inert organic solvent in the presence of tri($C_1$–$C_6$)alkylamine, the treatment of the reaction product with a boron hydride compound, and, if necessary, additional reactions such as deprotecting reaction, hydrolysis reaction, and salt-forming reaction, to prepare prostacyclics expressed by the following formula (II)

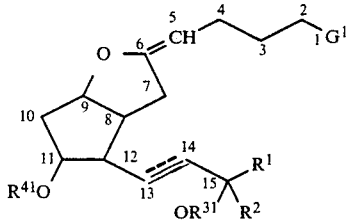

(II)

wherein the symbol ≡≡≡ between the 13- and 14-positions, $R^1$ and $R^2$ are as defined above; $G^1$ is as same as G or represents a carboxyl group or its salt; $R^{31}$ and $R^{41}$ are respectively as same as $R^3$, $R^4$ or represent a hydrogen atom.

DETAILED DESCRIPTION OF THE PREFERRED EMBODIMENTS

In the structure of 5,6-dehydroprostaglandins $F_2$ of the aforementioned formula (I) which is the material compound in the process for the preparation of prostacyclins of this invention, the four carbon atoms (at the 8-, 9-, 11-, and 12-positions) of the cyclopentane ring and the carbon atom at the 15-position are asymmetric carbon atoms. 5,6-Dehydroprostaglandins $F_2$ used in this invention contains all types of diastereomers and epimers due to the abovementioned asymmetric carbon atoms, except for a case in which the bonds (substituent groups) at the 8- and 9-positions in the cyclopentane ring are in a trans-relationship. Since the chemical reactions in the process proposed in the present invention are mostly proceeded without causing a conversion of steric configuration, the obtained prostacyclins expressed by formula (II) result in having the same configuration as the material compound, i.e. 5,6-dehydroprostaglandins $F_2$ expressed by formula (I). Therefore, in order to obtain prostacyclins having a configuration of natural type, natural type-5,6-dehydroprostaglandins $F_2\alpha$ expressed by the following formula (I')

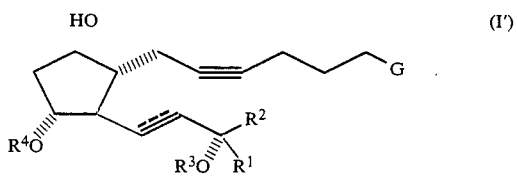

(I')

wherein the symbol ≡≡≡, G, $R^1$, $R^2$, $R^3$ and $R^4$ are as defined above,
are desirable to be used as 5,6-dehydroprostaglandins $F_2$.

The 5,6-dehydroprostaglandins $F_2$ of formula (I) which are used as material compounds can be conveniently prepared according to the method shown below.

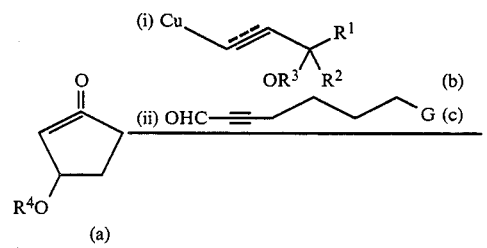

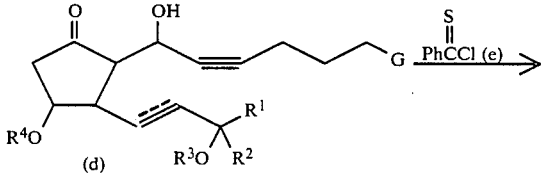

(d)

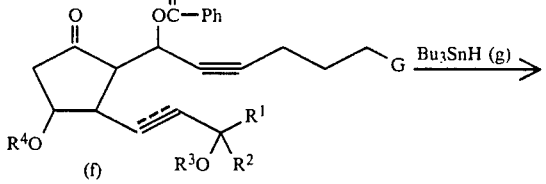

(f)

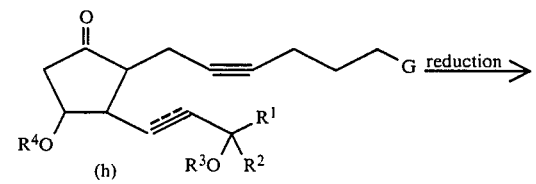

(h)

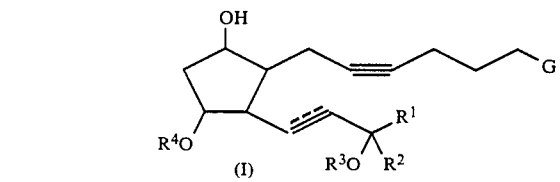

(I)

The 7-hydroxy-5,6-dehydroprostaglandins E of formula (d) can be produced by a process comprising reacting the corresponding cyclopent-2-en-1-ones of formula (a) with the corresponding organolithium compounds in the presence of cuprous salts and reacting the resulting β-substituted enolates with the corresponding aldehydes of formula (c) in accordance with the method described in the specification of U.S. Pat. No. 4,315,032. The obtained 7-hydroxy-5,6-dehydroprostaglandins E is allowed to react with thiobenzoyl chloride of formula (e) to obtain corresponding 7-substituted-5,6-dehydroprostaglandins E of formula (f), which is then treated with tributyltin hydride of formula (g) to give 5,6-dehydroprostaglandins E of formula (h). The 5,6-dehydroprostaglandins $F_2$ of formula (I) which are the material compounds of the present invention can be obtained by subjecting thus prepared 5,6-dehydroprostaglandins E of formula (h) to the reduction reaction.

In the formula (I), the symbol ≡≡≡ between the 13- and 14-positions represents a double or triple bond.

In the formula (I), G represents —COOR$^5$ or —CONR$^6$R$^7$. R$^5$ represents a $C_1$–$C_{10}$ alkyl group, a substituted or unsubstituted phenyl group, a substituted or unsubstituted alicyclic group, a substituted or unsubstituted phenyl ($C_1$–$C_2$) alkyl group or a tri($C_1$–$C_7$)hydrocarbon-silyl group.

Examples of the $C_1$–$C_{10}$ alkyl group include linear or branched alkyl groups of 1 to 10 carbon atoms, such as methyl, ethyl, n-propyl, iso-propyl, n-butyl, sec-butyl, tert-butyl, n-pentyl, n-hexyl, n-heptyl, n-octyl, n-nonyl and n-decyl.

Examples of suitable substituents for the substituted phenyl group are halogen atoms, a hydroxyl group, $C_2$–$C_7$ acyloxy groups, $C_1$–$C_4$ alkyl groups which may be halogenated, $C_1$–$C_4$ alkoxy groups which may be halogenated, a nitrile group, a carboxyl group and ($C_1$–$C_6$)alkoxycarbonyl groups. The halogen atoms are fluorine, chlorine and bromine atoms, and fluorine and chlorine atoms are preferred. Examples of the $C_2$–$C_7$ acyloxy groups are acetoxy, propionyloxy, n-butyryloxy, iso-butyryloxy, n-valeryloxy, iso-valeryloxy, caproyloxy, enanthyloxy or benzoyloxy.

Examples of suitable $C_1$–$C_4$ alkyl groups which may be halogenated include methyl, ethyl, n-propyl, iso-propyl, n-butyl, chloromethyl, dichloromethyl, and tri-fluoromethyl.

Examples of suitable $C_1$–$C_4$ alkoxy groups which may be halogenated include methoxy, ethoxy, n-propox, iso-propoxy, n-butoxy, chloromethoxy, dichloromethoxy, tri-fluoromethoxy.

Examples of the ($C_1$–$C_6$)alkoxycarbonyl group are methoxycarbonyl, ethoxycarbonyl, butoxycarbonyl and hexyloxycarbonyl.

The substituted phenyl group may contain 1 to 3, preferably 1, substituents exemplified above.

The substituted or unsubstituted alicyclic group may be a saturated or unsaturated $C_5$–$C_8$, preferably $C_5$–$C_6$, especially preferably $C_6$ group, such as cyclopentyl, cyclohexyl, cyclohexenyl, cycloheptyl, or cyclooctyl, which is unsubstituted or substituted by the same substituents as exemplified thereabove.

Examples of suitable tri($C_1$–$C_7$)hydrocarbonsilyl groups include tri($C_1$–$C_4$)alkylsilyl groups such as trimethylsilyl, triethylsilyl or t-butyldimethylsilyl, ($C_1$–$C_4$)alkyldiphenylsilyl groups such as t-butyldiphenylsilyl, and a tribenzylsilyl group.

$R^6$ and $R^7$ are identical or different and each represents a $C_1$–$C_{10}$ alkyl group, or taken together with the nitrogen atom to which they are bonded may form a substituted or unsubstituted 5- or 5-membered ring which may include a hetero atom. Specific examples of the $C_1$–$C_{10}$ alkyl group are the same as those exemplified hereinabove with regard to $R^5$.

Examples of the substituent for the substituted 5- or 6-membered ring may be those exemplified hereinabove. The hetero atom is, for example, nitrogen, sulfur or oxygen atoms. Examples of the ring are 1-pyrrolidyl, thiazolyl, 1-piperidyl, morpholyl, piperadyl and dibenzopiperidyl each as 5,6-dihydrophenanthridyl. G is preferably —COOR$^5$ in which $R^5$ represents a $C_1$–$C_{10}$ alkyl group.

In the formula (I), $R^1$ represents a hydrogen atom, a methyl group, or a protected ethynyl group. Examples of the protecting group indlude trimethylsilylethynyl and t-butyldimethylsilyl ethynyl. $R^1$ is preferably a hydrogen atom or a methyl group.

In the formula (I), $R^2$ represents an unsubstituted $C_5$–$C_8$ alkyl group; a substituted $C_1$–$C_5$ alkyl group substituted by a substituent selected from a phenyl group, a phenoxy group, a $C_1$–$C_6$ alkoxy group and a $C_5$–$C_6$ cycloalkyl group, which substituent may be substituted; or a substituted or unsubstituted alicyclic group. The unsubstituted $C_5$–$C_8$ alkyl group may be linear or branched, and includes, for example, n-pentyl, n-hexyl, 2-methyl-1-hexyl, 2-methyl-2-hexyl, n-heptyl, and n-octyl. The n-pentyl, n-hexyl, 2-methyl-1-hexyl, and 2-methyl-2-hexyl are preferred. The substituted $C_1$–$C_5$ alkyl group may be linear or branched, and includes, for example, methyl, ethyl, n-propyl, iso-propyl, n-butyl, sec-butyl, t-butyl and n-pentyl. These alkyl groups are substituted by a phenyl group; a phenoxy group; a $C_1$–$C_6$ alkoxy group such as methoxy, ethoxy, n-propoxy, iso-propoxy, n-butoxy, iso-butoxy, t-butoxy, n-pentoxy, or n-hexoxy; or a $C_5$–$C_6$ cycloalkyl group such as cyclopentyl or cyclohexyl. These substituents may be substituted by the same substituents as cited hereinabove as the substituents for the substituted phenyl group of $R^5$.

Examples of preferred substituted $C_1$–$C_5$ alkyl groups are $C_1$–$C_2$ alkyl groups substituted by a phenoxy or phenyl group which may further be substituted by a chlorine or fluorine atom or a methyl, ethyl or trifluoromethyl group; and propoxymethyl, ethoxyethyl, propoxyethyl, butoxymethyl, methoxypropyl, 2-ethoxy-1,1-dimethylethyl, propoxydimethylmethyl, cyclohexylmethyl, cyclohexylethyl, cyclohexyldimethylmethyl and 2-cyclohexyl-1,1-dimethylethyl. The substituted or unsubstituted alicyclic group may include the same species as cited with regard to $R^5$.

Preferably, $R^2$ is n-pentyl, n-hexyl, 2-methyl-1-hexyl, 2-methyl-2-hexyl, cyclopentyl, or cyclohexyl.

$R^3$ and $R^4$ are identical or different, and each represents a $C_2$–$C_7$ acyl group, a tri($C_1$–$C_7$)hydrocarbonsilyl group or a group forming an acetal linkage together with the oxygen atom of the hydroxyl group. Examples of the $C_2$–$C_7$ acyl group are acetyl, propionyl, n-butyryl, iso-butyryl, n-valeryl, iso-valeryl, caproyl, ethanthyl and benzoyl. Of these, $C_2$–$C_6$ aliphatic acyl groups such as acetyl, n- or iso-butyryl, caproyl and benzoyl are preferred. Examples of the tri($C_1$–$C_7$)hydrocarbonsilyl group are the same as those exemplified hereinabove with regard to $R^5$. Examples of the group forming an acetal linkage with the oxygen atom of the hydroxyl group are methoxymethyl, 1-ethoxyethyl, 2-methoxy-2-propyl, 2-ethoxy-2-propyl, (2-methoxyethoxy)methyl, benzyloxymethyl, 2-tetrahydropyranyl, 2-tetrahydrofuranyl and 6,6-dimethyl-3-oxa-2-oxo-bicyclo[3.1.0]hex-4-yl. Of these, 2-tetrahydropyranyl, 2-tetrahydrofuranyl, 1-ethoxyethyl, 2-methoxy-2-propyl, and (2-methoxyethoxy)methyl, and 6,6-dimethyl-3-oxa-2-oxo-bicyclo[3.1.0]hex-4-yl are preferred.

It should be understood that the hydrocarbonsilyl group, the acyl group and the group forming an acetal linkage are protective groups for the hydroxyl group. The hydrocarbon-silyl group or the acetal-forming group can be easily removed under acidic to neutral conditions. The acyl group can be easily removed under basic conditions.

Preferred as $R^3$ or $R^4$ are a tri($C_1$–$C_4$)alkylsilyl group, a ($C_1$–$C_4$)alkyldiphenyl silyl group, a 2-tetrahydropyranyl group, a 2-tetrahydrofuranyl group, a 1-ethoxyethyl group, a 2-ethoxy-3-propyl group, a (2-methoxyethoxy)methyl group, a 6,6-dimethyl-3-oxa-2-oxo-bycyclo[3.1.0]hex-4-yl group, an acetyl group, and a benzoyl group.

In the present invention, the desired prostacyclins expressed by the aforementioned formula (II) can be obtained by allowing the 5,6-dehydroprostaglandins F$_2$ expressed by the aforementioned formula (I) to react with a mercury (II) compound in an inert organic solvent in the presence of tri($C_1$–$C_6$)alkylamine and then treating the reaction product with a boron hydride compound, if necessary, followed further by the deprotecting reaction, hydrolysis reaction, or salt-forming reaction.

As the inert organic solvent to be used in this case, aprotic solvents including, for instance, such ethereal organic solvents as ethyl ether, isopropyl ether, tetrahydrofurane, dioxane, dimethoxyethane, etc. and such halogenated hydrocarbons as chloroform, methylene chloride, carbon tetrachloride, etc. can be used desirably. These inert organic solvents can also be used as a mixed solvent consisting of two or more solvents.

As the mercury (II) compounds, mercury (II) carboxylate, mercury (II) sulfonate, halogenated mercury (II) species, and mercury (II) oxides are desirably used. As the mercury (II) carboxylate, mercury acetate, mercury trifluoroacetate, etc. may be mentioned. As the mercury (II) sulfonate, there are mercury methansulfonate, mercury trifluoromethanesulfonate, etc. As the halogenated mercury (II) species, mercury chloride, mercury bromide, mercury iodide, etc., for instance, may be cited. Of all these, mercury acetate, mercury trifluoroacetate, and mercury chloride are preferable.

The quantity of the mercury (II) compound to be used in the reaction is equimolar with the material compound 5,6-dehydroprostaglandine $F_2$ expressed by the aforementioned formula (I) stoichiometrically; however, in the actual reaction 0.5 to 10 moles, preferably 0.8 to 3 moles, of mercury compound to 1 mole of 5,6-dehydroprostaglandin $F_2$ is used.

Tri($C_1$-$C_6$)alkylamine is used together with such mercury (II) compounds. As the tri($C_1$-$C_6$)alkylamine trimethylamine, triethylamine, tripropylamine, tributylamine, etc. may be mentioned and, of them all, trimethylamine is desirable. The amount of tri($C_1$-$C_6$)alkylamine to be used may be equimolar with the mercury (II) compound which takes part in the reaction; however, in the actual reaction, 0.1 to 10 moles, preferably 0.5 to 3 moles, of tri($C_1$-$C_6$)alkylamine to 1 mole of 5,6-dehydroprostaglandin $F_2$ expressed by the aforementioned formula (I), which is used as the material compound in the reaction, is recommendable.

The reaction temperature is usually selected within the range of $-150°$ C. to $100°$ C. and preferably within the range of $-80°$ C. to $-10°$ C. The reaction time usually ranges from 5 minutes to 2 hours.

The reaction is initiated with the addition of a material compound or a solution, which is prepared by dissolving the material compound in the same inert organic solvent mentioned above as the one used to dissolve a mercury (II) compound or in the different one, to an inert organic solvent, selected likewise from among the abovementioned inert organic solvents, in which the mercury (II) compound and tri($C_1$-$C_6$)alkylamine are made to exist dissolved, and vice versa in said way of addition. This first stage of the reaction is regarded to form an intermediate product expressed by the following formula (A)

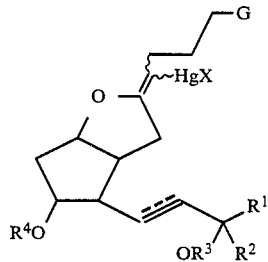
(A)

wherein the symbol ≡≡≡, G, $R^1$, $R^2$, $R^3$, and $R^4$ are as defined hereinabove and X indicates a counter anion of mercury.

After the reaction of the 5,6-dehydroprostaglandins $F_2$ of formula (I) with murcury (II) compounds in an inert organic solvent is carried out in the presence of tri($C_1$-$C_6$)alkylamine as described above, the obtained reaction product is treated with a boron hydride compound. It is assumed that the HgX groups of the compound of formula (A) are eliminated reductively in this treatment.

As the boron hydride compound to be used in said treatment, such boron hydride compounds as expressed by the following formula (III)

$$M(R^8)_{4-m}BH_m \qquad (III)$$

wherein M is an alkali metal atom, $R^8$ is a $C_1$-$C_6$ alkyl group, $C_1$-$C_6$ alkoxy group or cyano group, and m is an integer of 1 to 4, are desirable. M indicates an alkali metal atom and such alkali metal atoms as sodium, potassium, and lithium, for instance, may be mentioned as desirable ones. $R^8$ indicates a a $C_1$-$C_6$ alkyl group, $C_1$-$C_6$ alkoxy group or cyano group. Examples of the $C_1$-$C_6$ alkyl groups include methyl, ethyl, n-propyl, n-butyl, sec-butyl, n-pentyl groups (amyl groups), etc. As examples of the $C_1$-$C_6$ alkoxy groups, methoxy, ethoxy, propoxy, butoxy groups, for instance, may be mentioned as desirable ones.

As the boron hydride compounds, sodium boron hydride, lithium boron hydride, lithium triethylboron hydride, sodium triethylboron hydride, sodium tri-sec-butylboron hydride, lithium tri-sec-butylboron hydride, potassium tri-sec-butylboron hydride, potassium trisamylboron hydride, sodium trimethoxyboron hydride, lithium trimethoxyboron hydride, sodium triethoxyboron hydride, lithium triethoxyboron hydride, sodium tripropoxyboron hydride, sodium cyanoboron hydride, etc. may be mentioned. Of these boron hydride compounds mentioned above, sodium boron hydride, sodium trimethoxyboron hydride, and sodium triethoxyboron hydride may be described as desirable ones and sodium boron hydride is especially desirable.

The amount of these boron hydride compounds are usually used in the ratio of 0.5 to 50 moles, preferably 2 to 20 moles, to 1 mole of 5,6-dehydroprostaglandins $F_2$ of formula (I).

The treatment of the intermediate reaction product with a boron hydride compound is carried out following the procedure mentioned below.

After the first stage of the reaction is over, the inert organic solvent used in this first stage is removed from the reaction solution by distillation under reduced pressure or any other means. Then a solution prepared by dissolving a boron hydride compound in a protonic solvent such as methyl alcohol, ethyl alcohol, isopropyl alcohol, and water, or a mixture thereof is added to the residual reaction product. Or, such a solution of protonic solvent containing a boron hydride compound dissolved therein may be added to the reaction solution after the first stage of the reaction is over without removing the inert organic solvent therefrom. In this case, it is desirable to use a protonic solvent ⅓ to 10 times (by volume) the inert organic solvent used in the first stage. In case where water is used as a protonic solvent, the water may be adjusted to alkaline, for instance, with the use of sodium hydroxide.

In the present invention, it is advisable to use the boron hydride compound together with an alkali metal ($C_1$-$C_{10}$)alkoxide. As the alkali metal ($C_1$-$C_{10}$)alkoxide, sodium methoxide, sodium ethoxide, sodium propoxide, and sodium butoxide, for instance, may be mentioned and, of these mentioned above, sodium methoxide, and sodium ethoxide are preferable. The amount of the alkali metal (C$_1$–C$_{10}$) alkoxide to be used is usually 0.1 to 50 moles, preferably 0.9 to 20 moles to 1 mole of the boron hydride compound.

The reaction temperature at the treatment with a boron hydride compound is usually in the range of $-150°$ to $100°$ C., preferably $-80°$ to $-10°$ C., and the reaction time is usually in the range of 30 minutes to 24 hours.

The aftertreatment of the resulting reaction solution thus obtained may be carried out according to the usual method. For example, such an organic solvent insoluble in water as hexane, pentane, petroleum ether, ethyl ether, etc. is added to the reaction mixture or the reaction mixture is first concentrated under reduced pressure and then followed by addition of the abovementioned organic solvent insoluble in water to obtain an organic mixture. The obtained organic mixture is then washed with a saline water, dried with a desicating agent such as magnesium sulfate anhydride, sodium sulfate anhydride, potassium carbonate anhydride, etc., and has the organic solvent removed under reduced pressure to obtain a crude reaction product. With the purpose of maintaining the stability of the obtained prostacyclins during the aftertreatment, it is advisable to add such amines as triethylamine and trimethylamine to the reaction mixture. The crude reaction product can be purified by column chromatography, thin-layer chromatography, liquid chromatography, etc., preferably by column chromatography in an atmosphere made basic with triethylamine or any other similar amine depending upon requirements. Thus purified product can further be subjected to the deprotecting reaction, hydrolysis reaction, or salt-forming reaction as case may require.

When the protective group for the hydroxyl group is a group which forms an acetal linkage together with the oxygen atom of the hydroxyl group, the deprotection can be conveniently carried out by use of acetic acid, p-toluenesulfonic acid, a pyridinium salt of p-toluenesulfonate or a cation exchange resin as a catalyst and water, tetrahydrofuran, ethyl ether, dioxane, methanol, ethanol, acetone acetonile or the like as a reaction solvent. The reaction is usually carried out at a temperature of $-78°$ C. to $+30°$ C. for 10 minutes to about 3 days. When the protective group is a tri(C$_1$–C$_7$)hydrocarbonsilyl group, the reaction may be carried out at the same temperature and for the same reaction time as those mentioned above by use of acetic acid, hydrofluoric acid, tetrabutyl ammonium fluoride cesium fluoride, etc. as the catalyst.

When the protective group is an acyl group, the deprotecting reaction can be carried out by causing hydrolysis in an aqueous solution of sodium hydroxide, potassium hydroxide, calcium hydroxide, etc., a mixed solution of water and alcohol, or a methanol or ethanol solution containing sodium methoxide, potassium methoxide, sodium methoxide, etc.

The hydrolysis reaction can be carried out by use of such an enzyme as lipase in water or a water-containing solvent at a temperature of $-10°$ C. to $+60°$ C. approximately for 10 minutes to 24 hours.

According to this invention, the compound having a carboxyl group resulting from the above deprotecting reaction may, if required, be subjected to a salt-forming reaction to form the corresponding carboxylate salt. The salt-forming reaction is known per se, and can be carried out by neutralizing the carboxylic acid with a nearly equivalent amount of a basic compound such as sodium hydroxide, potassium hydroxide, sodium carbonate, ammonia, trimethylamine, monoethanolamine, or morpholine in a usual manner.

After the deprotecting reaction, hydrolysis reaction, or salt-forming reaction, the reaction product may be purified according to the same purifying method as mentioned above.

In this way, the desired prostacyclins expressed by the following formula (II)

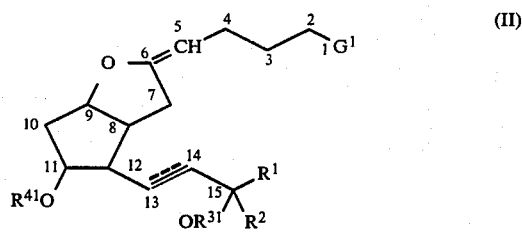

wherein the symbol ==== between the 13- and 14-positions, R$^1$ and R$^2$ are as defined above; G$^1$ is as same as G or represents a carboxyl group or its salt; R$^{31}$ and R$^{41}$ are respectively as same as R$^3$, R$^4$ or represent a hydrogen atom, is obtained.

The following compounds may be given as concrete examples of prostacyclins prepared according to the process proposed by the present invention.

(100) prostacyclin
(102) 16,17,18,19,20-pentanor-15-cyclopentylprostacyclin
(104) 16,17,18,19,20-pentanor-15-cyclohexylprostacyclin
(106) 17(R),20-dimethylprostacyclin
(108) 15-methylprostacyclin
(110) 20-methylprostacyclin
(112) 17,18,19,20-tetranor-16-phenoxyprostacyclin
(114) 17,18,19,20-tetranor-16-(p-chlorophenoxy)-prostacyclin
(116) 17(S),20-dimethylprostacyclin
(118) 17,18,19,20-tetranor-16-(m-flurorophenoxy)-prostacyclin
(120) 18-oxa-prostacyclin
(122) 13,14-dehydroprostacyclin
(124) 16-methylprostacyclin
(126) 13,14-dehydro-20-methylprostacyclin
(128) methyl ester of (100)
(130) methyl ester of (102)
(132) methyl ester of (104)
(134) ethyl ester of (106)
(136) n-butyl ester of (108)
(138) n-propyl ester of (110)
(140) sodium salt of (112)
(142) sodium salt of (114)
(144) potassium salt of (100)
(146) potassium salt of (102)
(148) calcium salt of (104)

$\Delta^6$-Prostaglandins I$_1$, which are isomers of the prostacyclins, can be obtained by allowing 5,6-dehydroprostaglandins F$_2$ of formula (I) to react with a mercury (II) compound in an inert organic solvent in the absence of tri(C$_1$–C$_6$)alkylamine, then followed by the treatment with a boron hydride compound, instead of allowing 5,6-dehydroprostaglandins F$_2$ of formula (I) to react with a mercury (II) compound in an inert organic solvent in the presence of tri(C$_1$–C$_6$)alkylamine, then followed by the treatment with a boron hydride compound in the process of the present invention mentioned above.

The present invention also provides the following process, i.e. a process for the preparation of $\Delta^6$-prostaglandins $I_1$ expressed by the following formula (IV)

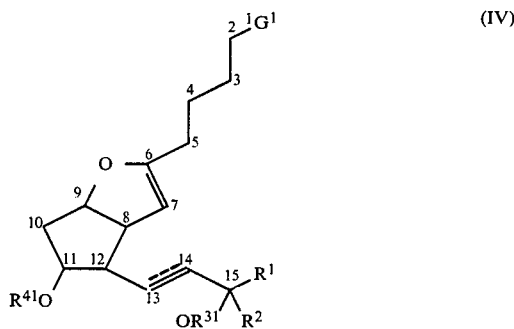

(IV)

wherein the symbol ≈≈≈, $G^1$, $R^1$, $R^2$, $R^{31}$ and $R^{41}$ are as defined above,
comprising allowing 5,6-dehydroprostaglandins $F_2$ expressed by the following formula (I)

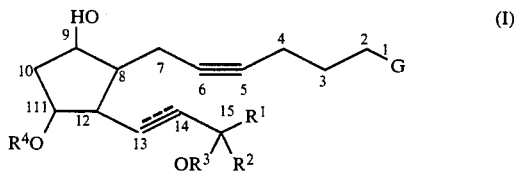

(I)

wherein the symbol ≈≈≈, G, $R^1$, $R^2$, $R^3$, and $R^4$ are as defined above,
to react with a mercury (II) compound in an inert organic solvent in the absence of tri($C_1$-$C_6$)alkylamine, treating the reaction product with a boron hydride compound, and subjecting the reaction product further to the deprotecting reaction, hydrolysis reaction, or salt-forming reaction as case may require.

As the inert organic solvent, mercury (II) compound, and boron hydride compound used in the abovementioned process are the same as those described hereinabove and they are used in the same way as above. The material compound 5,6-dehydroprostaglandins $F_2$ of formula (I) are the same as those described above.

In the abovementioned reaction, the reaction temperature at which the 5,6-dehydroprostaglandins $F_2$ are made to react with the mercury (II) compound is usually in the range of $-100°$ C. to $100°$ C., preferably in the range of $-10°$ C. to $50°$ C.

The reaction temperature at which the reaction product is treated with the boron hydride compound is in the range of $-50°$ C. to $100°$ C., preferably in the range of $-10°$ C. to $50°$ C.

Other reaction conditions are as same as those described above.

Thus obtained $\Delta^6$-prostaglandins $I_1$ themselves are compounds which have a valuable physiological action to inhibit the platelet aggregation and are further expected to display useful actions such as vasodilation, antitumor action, antiasmatic action, and anticancerous action, and they are also very useful as material compounds to be used for the preparation of prostacyclins which are more beneficial drugs (see I. Tömösközi et al., Tetrahedron Letters, 23, 1091–1094 (1982)).

As concrete examples of $\Delta^6$-prostaglandins $I_1$ which are prepared according to the present invention, the following compounds may be mentioned:
(200) $\Delta^6$-prostaglandin $I_1$
(202) 16,17,18,19,20-pentanor-15-cyclopentyl-$\Delta^6$-prostaglandin $I_1$
(204) 16,17,18,19,20-pentanor-15-cyclohexyl-$\Delta^6$-prostaglandin $I_1$
(206) 17(R),20-dimethyl-$\Delta^6$-prostaglandin $I_1$
(208) 15-methyl-$\Delta^6$-prostaglandin $I_1$
(210) 20-methyl-$\Delta^6$-prostaglandin $I_1$
(212) 13,14-dehydro-$\Delta^6$-prostaglandin $I_1$
(14) 18-oxa-$\Delta^6$-prostaglandin $I_1$
(216) 13,14-dehydro-20-methyl-$\Delta^6$-prostaglandin $I_1$
(218) methyl ester of (200)
(220) methyl ester of (202)
(222) ethyl ester of (204)
(224) sodium salt of (206)
(226) sodium salt of (208)

The process of this invention has its characteristic in that the process makes it possible to induce with ease a prostacyclin skeleton by the one-stage reaction from the material compounds of 5,6-dehydroprostaglandins $F_2$ which are easily available.

As described above, the process provided by the present invention has made it possible to achieve a simple and yet efficient method of preparing beneficial drugs of prostacyclin type and therefore has a great significance from the industrial viewpoint.

The following examples are illustrative of the present invention, but are not to be construed as limiting the scope of the present invention.

REFERENTIAL EXAMPLE

Synthesis of 5,6-dehydroprostaglandin $F_{2\alpha}$methyl ester 11,15-bis(t-butyldimethylsily)ether:

(i) 1.88 g (5.10 mmoles) of 1-iodo-3-(t-butyldimethylsilyloxy)-trans-1-octene was taken into a 150 ml reaction tube, and the inside of the reaction tube was purged with argon. Dry ether (20 ml) was added, and the mixture was cooled to $-78°$ C. To the solution was added 7.54 ml (10.4 mmoles) of a 1.38M pentane solution of t-butyl lithium, and the mixture was stirred for 2.5 hours. Separately, 971 mg (5.10 mmoles) of cuprous iodide was taken into a 30 ml test tube, and the inside of the flask was dried by heating under reduced pressure and then purged with argon. Dry ether (20 ml) and 2.54 ml (10.2 mmoles) of tributyl phosphine were added and the mixture was shaken to form a colorless clear solution. The solution was cooled to $-78°$ C., and added to the vinyl lithium solution prepared as above. The test tube was washed by using 20 ml of dry ether.

To the resulting organic copper reagent solution was added dropwise over 15 minutes 30 ml of a solution of 1.06 g (5.00 mmoles) of 4-(t-butyldimethylsilyloxy)-2-cyclopentenone in ether. The mixture was further stirred for 5 minutes. The temperature was raised to $-40°$ C., and the mixture was stirred for 15 minutes. Then, the solution was cooled to $-78°$ C., and 20 ml of a solution of 848 mg (5.50 mmoles) of 6-carbomethoxy-2-hexynal in ether was added, followed by stirring for 5 minutes. The temperature was again raised to $-40°$ C., and the mixture was stirred for 20 minutes. Then, 30 ml of a saturated aqueous solution of ammonium chloride was added, and the mixture was shaken vigorously to separate the ether layer. The aqueous layer was extracted with two 20 ml portions of ether. The etherial layers were combined and dried over anhydrous magnesium sulfate, and concentrated. The residue was chromatographed on a silica gel column (150 g) using hexane-ether (3:1) as an eluent to separate (7S) and (7R)-7-hydroxy-5,6-dehydro-PGE$_2$ methyl ester 11,15-bis-(t-butyldimethylsilyl)ethers [the total amount of (7S) and (7R) formed was 1.22 g; yield 39%].

(7S)-7-hydroxy-5,6-dehydro-PGE$_2$ methyl ester 11,15-bis-t-butyldimethylsilyl)ether:
  Rf=0.23 (hexane:ether=1:1)
  NMR (CDCl$_3$ δ ppm): 5.7–5.5 (m, 2H), 4.7–4.3 (br, 1H), 4.2–4.0 (m, 2H), 3.68 (s, 3H), 2.9–2.0 (m, 7H), 2.0–1.1 (m), 0.91 (s, 21H), 0.1–0.0 (m).
  IR (neat, cm$^{-1}$); 3500, 1746.

(7R)-7-hydroxy-5,6-dehydro-PGE$_2$ methyl ester 11,15-bis-(t-butyldimethylsilyl)ether:
  Rf=0.20 (hexane:ether=1:1)
  NMR (CDCl$_3$, δ ppm): 5.7–5.5 (m, 2H), 4.8–4.3 (br, 1H), 4.2–4.0 (m, 2H), 3.69 (s, 3H), 3.0–2.0 (m, 7H), 2.0–1.1 (m), 0.92 (m, 21H), 0.10–0.0 (m).
  IR (neat, cm$^{-1}$): 3494, 1748 Mass (20 eV, m/e): 590 (M+-18).

(ii) 200 mg (0.33 mmole) of 7-hydroxy-5,6-dehydroprostaglandin E$_2$ methyl ester 11,15-bis(t-butyldimethylsilyl)ether was didsolved in 20 ml of dry dichloromethane, and 136 mg (1.11 mmoles) of 4-dimethylaminopyridine was added. At 0° C., 160 mg (1.01 mmoles) of thiobenzoyl chloride was added by a syringe directly. The temperature of the mixture was raised to 18° C., and it was stirred for 3 hours. Dichloromethane (20 ml) was added to dilute the reaction mixture, and then it was washed with a 1N dilute aqueous solution of hydrochloric acid, water and a saturated aqueous solution of sodium bicarbonate. The washed product was dried over anhydrous sodium sulfate, and concentrated under reduced pressure. The residue was subjected to silica gel chromatography (10 g, ethyl acetate:hexane:benzene=1:15:2) to obtain a yellow oil (149.4 mg; 62.4%; low polarity). From $^1$H NMR, the main product, 7-phenylthiocarbonyloxy-5,6-dehydroprostaglandin E$_2$ methyl ester 11,15-bis(t-butyldimethylsilyl)ether, was determined to be a mixture of two stereoisomers. This is considered to be due to the steric configuration of C-7 and C-8 (threo and erythro forms).

The spectral data of the product are as follows:
  TLC: Rf=0.29 (hexane:ethyl acetate=5:1)
  IR (liquid film): 2230, 1743, 1596, 1210 cm$^{-1}$.
  $^1$H NMR(CDCl$_3$)δ: 0.1 and 0.17 (each S, 12, S.CH$_3$×4), 0.8–1.1 (m, 21, C-CH$_3$×7), 1.2–1.6 (m, 8, CH$_2$×4), 1.8–3.3 (m, 10, CH$_2$, CH$_2$CO×2, CH$_2$C≡, and CH×2), 3.74 (S, 3, OCH$_3$), 3.9–4.4 (m, 2, CHOSi×2), 5.6–5.8 (m, 2, vinyl), 6.37 and 6.66 (br, 1, CHOC(=S)), 7.3–7.6 (m, 3, phenyl), 8.1–8.4 (m, 2, phenyl).

(iii) 233.4 mg (0.32 mmole) of 7-phenylthiocarbonyloxy-5,6-dehydroprostaglandin E$_2$ methyl ester 11,15-bis(t-butyldimethylsilyl)ether was dissolved in 2 ml of tributyltin hydride in an atmosphere of argon, and 8 mg of bis-t-butyl peroxide was added. The mixture was stirred at 50° C. for 35 minutes. The reaction mixture was cooled to room temperature and directly chromatographed on a silica gel column (20 g of silica gel; ethyl acetate:hexane:benzene=1:15:2) to give 157.4 mg (83%) of 5,6-dehydroprostaglandin E$_2$ methyl ester 11,15-bis(t-butyldimethylsilyl)ether as a colorless oil.

The spectral data of the resulting product are shown below.

TLC: Rf=0.50 (ethyl acetate:hexane=1:5)
IR (neat): 1746, 1246, 827, 767 cm$^{-1}$.
$^1$H NMR (CDCl$_3$:CCl$_4$=1:1)δ: 0.04 and 0.06 (each s, 12, SiCH$_3$×2), 0.89 (s, 18, SiC(CH$_3$)$_3$×2), 0.92 (t, 1, J=6.5 Hz, CH$_3$), 1.1–1.5 (m, 8, CH$_2$×4), 1.7–2.9 (m, 12, CH$_2$CO×2, CH$_2$C≡×2, CH×2, and CH$_2$), 3.65 (s, 3, OCH$_3$), 4.05 (m, 2, CHOSi×2), 5.4–5.7 (m, 2, vinyl).
$^{13}$C NMR (DCDl$_3$) δ: −4.7, −45. (for two), −4.2, 13.6, 14.0, 16.9, 18.0, 18.2, 22.6, 24.2, 25.0, 25.8 (for three), 25.9 (for three), 31.9, 32.7, 38.6, 47.7, 51.4, 51.9, 52.9, 72.7, 73.1, 77.3, 80.8, 128.2, 136.8, 173.4, 213.4.
$[α]_D^{21}$: −13.9° (C=1.59, CH$_3$OH)

(iv) A solution of 25.5 mg (0.043 mmole) of 5,6-dehydroprostaglandin E$_2$ methyl ester 11,15-bis(t-butyldimethylsilyl)ether in 1 ml of toluene was added to a toluene solution (0.19M, 2.24 ml, 0.43 mmole) of diisobutyl aluminum hydride (1 equivalent)/2,6-di-t-butyl-4-methylpenol (2 equivalents). The mixture was stirred at −78° C. for 2 hours. Then, the temperature was raised, and the mixture was stirred at −25° to −20° C. for 3 hours. 10 ml of a saturated aqueous solution of sodium tartrate was added, and the mixture was vigorously shaken.

The reaction mixture was extracted three times with ethyl acetate (20+10+10 ml) at room temperature. The organic layers were combined, dried over anhydrous sodium sulfate, and concentrated under reduced pressure.

The residue was subjected to silica gel column chromatography (5 g; ethyl acetate:hexane=5:1) to obtain 23.5 mg (92%, less polar component) of 5,6-dehydroprostaglandin F$_{2α}$ methyl ester 11,15-bis(t-butyldimethylsilyl)ether.

The spectral data of the product are as follows:
TLC: Rf=0.29 (ethyl acetate:hexane=1:5).
IR (liquid film): 3640–3080, 1745, 1247, 1020, 970, 930, 830, 770 cm$^{-1}$.
$^1$H NMR (CDCl$_3$) δ: 0.02 and 0.05 (each s, 12, SiCH$_3$×4), 0.7–1.0 (m, 21, C—CH$_3$×7), 2.1–3.5 (m, 20, CH$_2$CO, CH$_2$×6, CH$_2$C≡×2, CH×2), 3.69 (d, 1, J=8.3 Hz, OH), 3.67 (s, 3, OCH$_3$), 4.00 and 4.24 (br, 3, CHO×3), 5.40 (m, 2, vinyl).
$[α]_D^{21}$: +0.37° (C=0.715, CH$_3$OH)

EXAMPLE 1

Synthesis of prostacyclin methyl ester 11,15-bis-t-butyldimethylsilyl ether 1.03 mg of 5,6-dihydroprostaglandin F$_{2α}$ methyl ester 11,15-bis-t-butyldimethylsilyl ether and 2 ml of anhydrous tetrahydrofuran (THF) were placed in a 20-ml test tube (oven-dried) filled with argon and cooled to −78° C. A solution prepared by dissolving 8.1 mg of mercury trifluoroacetate (Hg(OCOCF$_3$)$_2$) and 1.9 mg of triethylamine (Et$_3$N) in 2 ml of anhydrous THF was added thereto very slowly by using a stainless steel tube extending over a period of 5 minutes and the mixture was stirred at −78° C. for 1 hour. Then a solution prepared by dissolving 3.6 mg of sodium boron hydride in 0.19 ml of 1N MeONa/MeOH was added to the reaction mixture at a stretch with the use of a stainless steel tube. After the reaction mixture was stirred at −78° C. for 1 hour, 0.01 ml of triethylamine was added thereto, the temperature of the admixture was allowed to return to room temperature. The reaction solution was diluted with 10 ml of ether and poured into 10 ml of a saturated aqueous solution of sodium hydrogencarbonate. The mixture was stirred and mixed thoroughly and was then made to separate into a water layer and an organic layer. The water layer was extracted with 10 ml of ether. The extract was mixed with the organic layer and dried over anhydrous magnesium sulfate/anhydrous sodium carbonate (1:1). After the concentration was over, the reaction product was put to florisil column chromatography (n-hexane:ethyl acetate:Et$_3$N=40:1:0.1).

As the resulting product, 6.9 mg (yield 67%) of prostacyclin methyl ester 11,15-bis-t-butyldimethylsilyl ether. The spectral data of this product were in fair agreement with the spectral data of the authentic sample prepared from natural PGI$_2$. $(\alpha)_D^{21}=+28.8°$ C. (C 0.4 CHCl$_3$)

IR (CHCl$_3$): 1730, 1692 cm$^{-1}$ $^1$HNMR (CDCl$_3$) δ: 0.02, 0.03 (respectively s, 12, SiCH$_3$×4), 0.8–0.9 (21, SitBu×2, CH$_3$), 1.1–2.6 (m, 20, CH$_2$×9 and CH×9) 3.66 (s, 3, OCH$_3$), 3.7–4.2 (m, 3, >CHO—×2 and vinyl), 4.56 (br, 1, >CHO—), 5.46 (m, 2, vinyl)

EXAMPLE 2

Synthesis of prostacyclin methyl ester 11,15-bis-t-butyldimethylsilyl ether 7.9 mg of 5,6-dehydroprostaglandin F$_{2\alpha}$ methyl ester 11,15(RS)-bis-t-butyldimethylsilyl ether and 2 ml of anhydrous tetrahydrofuran were put in a 20-ml test tube (oven-dried) filled with argon, cooled to $-78°$ C., and stirred. A solution prepared by dissolving 5.7 mg of Hg(OCOCF$_3$)$_2$ and 1.3 mg of Et$_3$N in 2 ml of anhydrous tetrahydrofuran was added thereto slowly by use of a stainless steel tube and the mixture was stirred at $-78°$ C. for 1.5 hour.

Then 0.13 ml of 1N MeONa/MeOH containing 2.5 mg of NaBH$_4$ was added to the reaction mixture at a stretch by use of a stainless steel tube.

After the reaction mixture was stirred at $-78°$ C. for another 1.5 hour, 0.01 ml of Et$_3$N was added and the reaction solution was left to return to room temperature. Thereafter, the reaction solution was diluted with ether and decanted on a saturated aqueous solution of sodium bicarbonate. After the mixture was thoroughly shaked, the mixture was allowed to separate into a water layer and an organic layer and the water layer was extracted with ether. The extract was mixed with the organic layer and dried over a mixture of potassium carbonate and magnesium sulfate.

The reaxtion mixture was then put to Florisil column chromatography (n-hexane:ethylacetate:Et$_3$N=40:1:0.2) to elute the desired product. The obtained product was purified to give 5.1 mg (yield 65%) of prostacyclin methyl ester 11,15(RS)-bis-t-butyldimethylsilyl ether. This product gave the same spectral data as the product of Example 1.

EXAMPLE 3

Synthesis of prostacyclin methyl ester 1.9 mg of prostacyclin methyl ester 11,15-bis-t-butyldimethylsilyl eher was placed into a 5-ml test tube and 0.5 ml of THF and further 0.04 ml of tetrabutylammonium fluoride (n-Bu$_4$NF)(1M/THF) were added thereto. The mixture was stirred at room temperature (15° C.) for 12 hours. Then 0.04 ml of n-Bu$_4$NF(1M/THF) and a small quantity of triethylamine were further added to the reaction mixture and stirred for 3 hours. 0.5 ml of n-hexane (containing 0.1% triethylamine) was added to the reaction solution and concentrated. The concentrated solution was put to column chromatography (ethyl acetate:n-hexane=1:1, containing 0.1% Et$_3$N) to obtain 5.4 mg (yield 74%) of prostacyclin methyl ester as a resulting product. The spectral data of this substance were the same as those of prostacyclin methyl ester obtained from natural prostacylin. $(\alpha)_D^{21}=+79.8°$ C.(C 0.27, CHCl$_3$) mp: 35° C.

IR(CHCl$_3$): 3600, 3560–3280, 1730, 1695 cm$^{-1}$.

$^1$HNMR(CDCl$_3$) δ: 0.89 (t, 3, J=6.5 Hz, CH$_3$), 1.1–2.5 (m, 22, CH$_2$×9, CH×2, OH×2), 3.67 (s, 3, OCH$_3$), 3.7–4.2 (m, 3, >CHO—×3), 4.58 (m, 1, vinyl) 5.55 (m, 2, vinyl).

$^{13}$CNMR(CDCl$_3$) δ: 174.5, 154.6, 136.4, 131.8, 95.8, 83.4, 77.0, 73.0, 54.7, 51.4, 45.3, 40.6, 37.0, 33.6, 33.0, 31.7, 25.1, 24.7, 22.6, 14.0.

EXAMPLE 4

Synthesis of Δ$^6$-prostaglandin I$_1$ methyl ester 11,15-bis-t-butyldimethylsilyl ether 12.2 mg of 5,6-Dehydroprostaglandin F$_{2\alpha}$ methyl ester 11,15-bis-t-butyldimethylsilyl ether and 2 ml of anhydrous THF were put in a 20-ml test tube in which air had been replaced by argon and the content was cooled to 0° C. and stirred. Then 8.7 mg of Hg (OCOCF$_3$)$_2$ dissolved in 2 ml of anhydrous THF was added thereto slowly by use of a stainless steel tube and the mixture was stirred at 0° C. for 30 minutes. Thereafter, 0.2 ml of 1N MeONa/MeOH and 3.9 mg of NaBH$_4$ were added to the reaction mixture at a stretch by use of a stainless steel tube. After the reaction mixture were stirred at 0° C. for 1 hour, the mixture was diluted with ether and poured into a saturated aqueous solution of sodium bicarbonate. The mixture was then shaked thoroughly and was separated into a water layer and an organic layer. The water was extracted with ether. The extract was mixed with the organic layer and dried over a mixture of potassium carbonate and magnesium sulfate. After the reaction product was concentrated, it was purified by Florisil column chromatography (n-hexane:ethyl acetate:Et$_3$N=40:1:0.2) to give 6.5 mg (yield 53%) of Δ$^6$-prostaglandin I$_1$ methyl ester 11,15-bis-t-butyldimethylsilyl ether.

$^1$HNMR (CDCl$_3$) δ: 0.02, 0.04 (respectively 2, 12, SiCH$_3$×4), 0.8–0.9 (21, SiC(CH$_3$)$_3$×2 and CH$_3$), 1.1–3.0 (m, 20, CH$_2$×9 and CH×2), 3.67 (s, 3, OCH$_3$), 3.7–4.1 (m, 2, CHO—X$_2$), 4.60 (br, 1, CHO—), 4.70 (m, 1, vinyl), 5.45 (m, 2, vinyl).

EXAMPLE 5

Synthesis of Δ$^6$-prostacyclin I$_1$ methyl ester 6 mg of Δ$^6$-prostaglandin I$_1$ methyl ester 11,15-bis-t-butyldimethylsilyl ether was weighed and dissolved in 0.5 ml of anhydrous tetrahydrofuran, and 0.05 ml of n-Bu$_4$NF (1M/THF) and 10 μl of triethylamine were added thereto, and the mixture was stirred at room temperature (20° C.) for 1 hour. 0.5 ml of hexane containing 0.1% triethylamine was added to the reaction solution and the mixture was concentrated. The concentrate was put to column chromatography (ethyl acetate:n-hexane=1:1, containing 0.1% Et$_3$N) to give 2.7 mg (yield 75%) of Δ$^6$-prostaglandin I$_1$ methyl ester as a final product. The spectral data of this product were in agreement with those described in the document.

$^1$HNMR (CDCl$_3$) δ3.65 (s, 3, OM$_e$), 4.65 (d, 1, C$_7$ vinyl H, J=2.5 Hz).

EXAMPLE 6

Synthesis of 16,17,18,19,20-pentanor-15-cyclopentylprostacyclin methyl ester 11,15-bis-t-butyldimethylsilyl ether 20 mg of 16,17,18,19,20-pentanor-15-cyclopentyl-5,6-dehydroprostaglandin $F_{2\alpha}$ methyl ester 11,15-bis-t-butyldimethylsilyl ether and 3 ml of anhydrous tetrahydrofuran (THF) were placed in a 30 ml test tube (oven-dried) filled with argon and cooled to $-78°$ C. A solution of 19 mg of mercuric trifluoroacetate [Hg(OCOCF$_3$)$_2$] and 4.1 mg of triethylamine (Et$_3$N) in 2 ml of anhydrous tetrahydrofuran was added slowly over a period of 5 minutes and the mixture was stirred at $-78°$ C. for 1 hour. A solution of 7.8 mg of sodium boron hydride in 0.41 ml of 1N MeONa—MeOH was added to the reaction mixture at a strech. After the reaction mixture was stirred at $-78°$ C. for 1 hour, 0.01 ml of triethylamine was added, and the temperature was allowed to return to room temperature. The reaction solution was diluted with 15 ml of ether and poured into 15 ml of a saturated aqueous solution of sodium hydrogencarbonate. The mixture was stirred thoroughly and then separated into a water layer and an organic layer. The water layer was extracted with 15 ml of ether. The extract was combined with the organic layer and dried over anhydrous magnesium sulfate-anhydrous sodium carbonate (1:1). The soluvent was distilled off under reduced pressure. The residue was purified by Florisil column chromatography (n-hexane:ethylacetate:Et$_3$N=40:1:0.1) to give 12 mg (yield 60%) of 16,17,18,19,20-pentanor-15-cyclopentylprostacyclin methyl ester 11,15-bis-t-butyldimethylsilyl ether.

IR(CHCl$_3$): 1732, 1692 cm$^{-1}$.

$^1$H NMR(CDCl$_3$) δ: 0.01-0.03 (12, SiCH$_3$33 4) 0.8-1.0 (18, SitBu×2) 1.1-2.5 (m, 21, CH$_2$×9 and CH×3) 3.66 (s, 3, OCH$_3$), 3.7-4.3 (m, 3, >CHO— and vinyl), 4.59 (br, 1, >CHO—), 5.46 (m, 2, vinyl).

EXAMPLE 7

Synthesis of 17(S),20-dimethylprostacyclin methyl ester 11,15-bis-t-butyldimethylsilyl ether 21 mg of 17(S),20-dimethyl-5,6-dehydroprostaglandin $F_{2\alpha}$ methyl ester 11,15-bis-t-butyldimethylsilyl ether and 3 ml of anhydrous tetrahydrofuran were placed in a 30 ml test tube (oven-dried) filled with argon and cooled to $-78°$ C. A solution of 19 mg of mercuric trifluoroacetate and 4.1 mg of triethylamine in 2 ml of anhydrous tetrahydrofuran was added slowly over a period of 5 minutes and the mixture was stirred at $-78°$ C. for 1 hour. A solution of 7.8 mg sodium boron hydride in 0.41 ml of 1N MeONa—MeOH was added to the reaction mixture at a strech. After the reaction mixture was stirred at $-78°$ C. for 1 hours, 0.01 ml of triethylamine was added, and the temperature was allowed to return to room temperature. The reaction solution was diluted with 15 ml of ether and poured into 15 ml of a saturated aqueous solution of sodium hydrogencarbonate. The mixture was stirred thoroughly and then separated into a water layer and an organic layer. The water layer was extracted with 15 ml of ether. The extract was combined with the organic layer and dried over anhydrous magnesium sulfate-anhydrous sodium carbonate (1:1). The solvent was distilled off under reduced pressure. The residue was purified by Florisil column chromatography (n-hexane:ethylacetate:Et$_3$N=40:1:0.1) to give 13.3 mg (yield 63%) of 17(S),20-dimethylprostacyclin methyl ester 11,15-bis-t-butyldimethylsilyl ether.

IR(CHCl$_3$): 1730, 1692 cm$^{-1}$.

$^1$H NMR(CDCl$_3$) δ: 0.01-0.02 (12, SiCH$_3$×4), 0.8-1.0 (24, SitBu×2, CH$_3$×2), 1.1-2.6 (21, CH$_2$×9, CH×3), 3.66 (s, 3, OCH$_3$), 3.7-4.3 (m, 3, >CHO—×2 and vinyl), 4.59 (br, 1, >CHO—), 5.46 (m, 2, vinyl).

EXAMPLE 8

Synthesis of 16,17,18,19,20-pentanor-15-cyclopentylprostacyclin methyl ester 12 mg of 16,17,18,19,20-pentanor-15-cyclopentylprostacyclin methyl ester 11,15-bis-t-butyldimethylsilyl ether was dissolved in 0.5 ml of tetrahydrofuran. 0.08 ml of tetrabutylammonium fluoride (1M/THF) and triethylamine was added and the mixture was stirred for 14 hours. 0.5 ml of n-hexane (containing 0.1% triethylamine) was added to the reaction mixture. The mixture was concentrated and the residue was purified by Fluorisil column chromatography (ethyl acetate:n-hexane=1:1, containing 0.1% Et$_3$N) to give 5.2 mg (yield 70%) of 16,17,18,19,20-pentanor-15-cyclopentylprostacyclin methyl ester.

IR(film): 3400, 1735, 1695 cm$^{-1}$.

$^1$H NMR(CDCl$_3$) δ: 1.1-2.8 (m, 23, CH$_2$×9 and CH×3,) H×2), 3.67 (s, 3,)CH$_3$), 3.7-4.25 (m, 3, >CHO—×2 and vinyl), 4.58 (br, 1, >CHO—), 5.55 (m, 2, vinyl).

EXAMPLE 9

Synthesis of 17(S),20-dimethylprostacyclin methyl ester 13 mg of 17(S),20-dimethylprostacyclin methyl ester 11,15-bis-t-butyldimethylsilyl ether was dissolved in 0.5 ml of tetrahydrofuran. 0.08 ml of tetrabutylammonium fluoride (1M/THF) and triethylamine was added and the mixture was stirred for 14 hours. 0.5 ml of n-hexane (containing 0.1% triethylamine) was added to the reaction mixture. The mixture was concentrated and the residue was purified by Florisil column chromatography (ethyl acetate:n-hexane=1:1, containing 0.1% Et$_3$N) to give 6.1 mg (yield 74%) of 17(S),20-dimethylprostacyclin methyl ester.

IR(film): 3400, 1735, 1695 cm$^{-1}$.

$^1$H NMR (CDCl$_3$) δ: 0.8-1.0 (m, 6, CH$_3$×2), 1.1-2.8 (m, 23, CH$_2$×9, CH×3, OH×2), 3.67 (s, 3, OCH$_3$), 3.7-4.25 (m, 3, >CHO— and vinyl), 4.57 (br, 1, >CHO—), 5.56 (m, 2, vinyl).

EXAMPLE 10

Synthesis of prostacyclin sodium salt 5 mg of prostacyclin methyl ester was stirred at room temperature for 8 hours in 0.2 ml of a 0.35M aqueous solution of sodium hydroxide and 0.2 ml of ethanol to prepare an aqueous solution of a sodium salt of prostacyclin.

EXAMPLE 11

Synthesis of 16,17,18,19,20-pentanor-15-cyclopentylprostacyclin sodium salt 16,17,18,19,20-Pentanor-15-cyclopentylprostacyclin methyl ester was hydrolyzed in the same way as in Example 10 to give an aqueous solution of a sodium salt of 16,17,18,19,20-pentanor-15-cyclopentylprostacyclin.

EXAMPLE 12

Synthesis of 17(S),20-dimethylprostacyclin sodium salt

17(S),20-Dimethylprostacyclin methyl ester was hydrolyzed in the same way as in Example 10 to give an aqueous solution of a sodium salt of 17(S),20-dimethylprostacyclin.

What we claim is:

1. A process for the preparation of a prostacyclin comprising the reaction of a 5,6-dehydroprostaglandin $F_2$ expressed by the following formula (I)

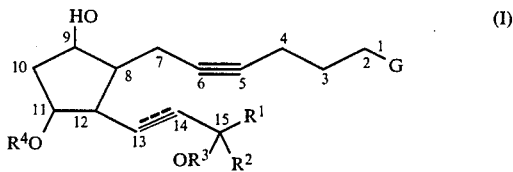

wherein the symbol ≡≡≡ between the 13- and 14-positions indicates that a double or triple bond exists between the 13- and 14-positions; G represents —COOR$^5$ or —CONR$^6$R$^7$ in which R$^5$ represents a $C_1$–$C_{10}$ alkyl group, a substituted or unsubstituted phenyl group, a substituted or unsubstituted alicyclic group, a substituted or unsubstituted phenyl ($C_1$–$C_2$) alkyl group or a tri($C_1$–$C_7$)hydrocarbonsilyl group, R$^6$ and R$^7$ are identical or different and each represents a $C_1$–$C_{10}$ alkyl group, taken together with a nitrogen atom to which they are bonded may form a substituted or unsubstituted 5- or 6-membered ring which may include a hetero atom; R$^1$ represents a hydrogen atom, a methyl group, or a protected ethynyl group; R$^2$ represents an unsubstituted $C_5$–$C_8$ alkyl group, a $C_1$–$C_5$ alkyl group substituted by a substituent selected from phenyl, phenoxy, $C_1$–$C_6$ alkoxy and $C_5$–$C_6$ cycloalkyl, which substituent may be substituted, or a substituted or unsubstituted alicyclic group; R$^3$ and R$^4$ are identical or different and each represents a $C_2$–$C_7$ acyl group, a tri($C_1$–$C_7$)hydrocarbon-silyl group or a group forming an acetal linkage together with the oxygen atom of the hydroxyl group,
with a mercury (II) compound in an inert organic solvent in the presence of tri($C_1$–$C_6$)alkylamine, the treatment of the reaction product with a boron hydride compound, and, if necessary, deprotecting reaction, hydrolysis reaction, or salt-forming reaction, to prepare a prostacyclin expressed by the following formula (II)

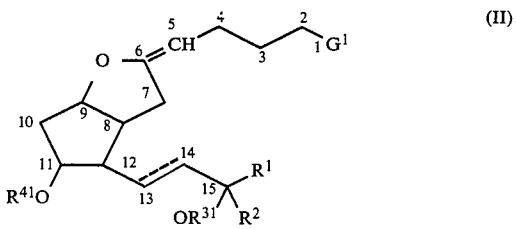

wherein the symbol ≡≡≡ between the 13- and 14-positions, R$^1$ and R$^2$ are as defined above; G$^1$ is as same as G or represents a carboxyl group or its salt; R$^{31}$ and R$^{41}$ are respectively as same as R$^3$, R$^4$ or represent a hydrogen atom.

2. A process for the preparation of a prostacyclin of claim 1, wherein said mercury (II) compound is the mercury (II) carboxylate, mercury (II) sulfonate, halogenated mercury (II) species, or mercury (II) oxides.

3. A process for the preparation of a prostacyclin of claim 2, wherein said mercury (II) carboxylate is mercury acetate or mercury trifluoroacetate.

4. A process for the preparation of a prostacyclin of claim 2, wherein said halogenated mercury (II) species is mercury chloride.

5. A process for the preparation of a prostacyclin of claim 1, wherein said boron hydride compound is a boron hydride compound expressed by the following formula (III)

$$M(R^8)_{4-m}BH_m \qquad (III)$$

wherein M is an alkali metal atom, R$^8$ is a $C_1$–$C_6$ alkyl group, $C_1$–$C_6$ alkoxy group or cyano group, and m is an integer of 1 to 4.

6. A process for the preparation of a prostacyclin of claim 5, wherein said boron hydride compound is sodium boron hydride, sodium trimethoxyboron hydride, or sodium triethoxyboron hydride.

7. A process for the preparation of a prostacyclin of claim 1, wherein said boron hydride compound is used together with an alkali metal ($C_1$–$C_{10}$) alkoxide.

8. A process for the preparation of a prostacyclin of claim 1, wherein said inert organic solvent is an aprotic solvent.

9. A process for the preparation of a prostacyclin of claim 1, wherein G is —COOR$^5$ in which R$^5$ represents a $C_1$–$C_{10}$ alkyl group.

10. A process for the preparation of a prostacyclin of claim 1, wherein R$^1$ represents a hydrogen atom or a methyl group.

11. A process for the preparation of a prostacyclin of claim 1, wherein R$^2$ represents n-pentyl, n-hexyl, 2-methyl-1-hexyl, 2-methyl-2-hexyl, cyclopentyl, or cyclohexyl group.

12. A process for the preparation of a prostacyclin of claim 1, wherein R$^3$ and R$^4$ each represents a tri($C_1$–$C_4$)alkylsilyl group, a ($C_1$–$C_4$)alkyldiphenylsilyl group, a 2-tetrahydropyranyl group, a 2-tetrahydrofuranyl group, a 1-ethoxyethyl group, a 2-ethoxy-2-propyl group, a (2-methoxyethoxy)methyl group, a 6,6-dimethyl-3-oxa-2-oxo-bycyclo[3,1,0]-hex-4-yl group, an acetyl group, and a benzoyl group.

13. A process for the preparation of Δ$^6$-prostaglandins I$_1$ expressed by the following formula (IV)

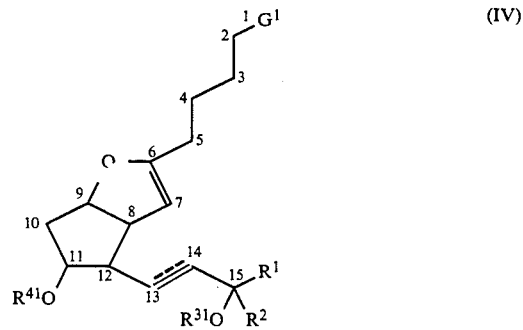

wherein the symbol ≡≡≡, G$^1$, R$^1$, R$^2$, R$^{31}$ and R$^{41}$ are as defined in claim 1, comprising allowing a 5,6-dehydroprostaglandin $F_2$ expressed by the following formula (I)

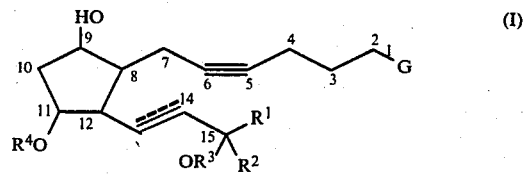

wherein the symbol ≡≡≡, G, $R^1$, $R^2$, $R^3$ and $R^4$ are as defined in claim 1, to react with a mercury (II) compound in an inert organic solvent in the absence of tri($C_1$-$C_6$)alkylamine, treating with the reaction product with a boron hydride compound, and, if necessary, further subjecting the reaction product to the deprotecting reaction, hydrolysis reaction, or salt-forming reaction.

* * * * *